United States Patent
Hamilton et al.

(10) Patent No.: US 6,793,661 B2
(45) Date of Patent: Sep. 21, 2004

(54) ENDOSCOPIC SHEATH ASSEMBLIES HAVING LONGITUDINAL EXPANSION INHIBITING MECHANISMS

(75) Inventors: Bruce Hamilton, Hampstead, NH (US); Mark S. Landman, Sharon, MA (US); Steve Martone, Westford, MA (US); Timothy J. Mulhern, Natick, MA (US)

(73) Assignee: Vision Sciences, Inc., Natick, MA (US)

( * ) Notice: Subject to any disclaimer, the term of this patent is extended or adjusted under 35 U.S.C. 154(b) by 6 days.

(21) Appl. No.: 10/313,848

(22) Filed: Dec. 5, 2002

(65) Prior Publication Data

US 2003/0083547 A1 May 1, 2003

Related U.S. Application Data

(63) Continuation-in-part of application No. 10/094,406, filed on Mar. 8, 2002, which is a continuation-in-part of application No. 09/702,155, filed on Oct. 30, 2000, now Pat. No. 6,461,294.

(51) Int. Cl.$^7$ .............................................. A61M 5/00
(52) U.S. Cl. ................... 606/116; 128/200.26; 600/108
(58) Field of Search ................................ 600/116, 115, 600/123, 114, 108, 96; 606/116, 192; 128/200.26, 207.15

(56) References Cited

U.S. PATENT DOCUMENTS

| | | | |
|---|---|---|---|
| 3,776,222 A | 12/1973 | Smiddy | |
| 4,066,070 A | 1/1978 | Utsugi | 128/4 |
| 4,148,307 A | 4/1979 | Utsugi | 128/4 |
| 4,176,662 A | 12/1979 | Frazer | 128/6 |
| 4,180,076 A | 12/1979 | Betancourt | 128/349 B |
| 4,224,929 A | 9/1980 | Furihata | 128/5 |
| 4,295,464 A | 10/1981 | Shihata | 128/1 R |
| 4,404,971 A | 9/1983 | LeVeen et al. | 128/348.1 |

(List continued on next page.)

*Primary Examiner*—Ehud Gartenberg
*Assistant Examiner*—Leonid M Fastovsky
(74) *Attorney, Agent, or Firm*—Dorsey & Whitney, LLP

(57) ABSTRACT

Methods and apparatus for inhibiting longitudinal expansion of a body portion of an endoscopic sheath during inflation of an inflatable member are disclosed. In one embodiment, a sheath assembly includes a body portion adapted to encapsulate a distal end of an insertion tube, and an inflatable member coupled to the body portion and adapted to be inflated radially outwardly from the body portion. The sheath assembly further includes an expansion-inhibiting mechanism coupled to at least one of the inflatable member and the body portion. The expansion-inhibiting mechanism advantageously inhibits a longitudinal expansion of the body portion during inflation of the inflatable member. The expansion-inhibiting mechanism may assume a variety of embodiments, including, for example, a non-compliant member, a longitudinally-stretched portion, a reinforcing spring member, a pressure relief device, or a suitable detent mechanism.

23 Claims, 10 Drawing Sheets

U.S. PATENT DOCUMENTS

| | | | | |
|---|---|---|---|---|
| 4,676,228 A | | 6/1987 | Krasner et al. | 600/116 |
| 4,690,131 A | | 9/1987 | Lyddy, Jr. et al. | 128/4 |
| 4,752,286 A | | 6/1988 | Okada | 604/96 |
| 4,892,099 A | | 1/1990 | Ohkawa et al. | 606/194 |
| 4,947,827 A | * | 8/1990 | Opie, deceased et al. | 600/108 |
| 4,976,261 A | * | 12/1990 | Gluck et al. | 128/207.15 |
| 5,025,778 A | | 6/1991 | Silverstein et al. | 600/104 |
| 5,078,681 A | | 1/1992 | Kawashima | 606/198 |
| 5,217,001 A | * | 6/1993 | Nakao et al. | 600/123 |
| 5,331,947 A | | 7/1994 | Shturman | 600/115 |
| 5,337,732 A | * | 8/1994 | Grundfest et al. | 600/116 |
| 5,400,770 A | * | 3/1995 | Nakao et al. | 606/116 |
| 5,419,310 A | | 5/1995 | Frassica et al. | 128/4 |
| 5,425,738 A | | 6/1995 | Gustafson et al. | 606/153 |
| 5,454,364 A | * | 10/1995 | Kruger | 600/114 |
| 5,569,161 A | | 10/1996 | Ebling et al. | 600/121 |
| 5,577,992 A | | 11/1996 | Chiba et al. | 600/152 |
| 5,628,753 A | | 5/1997 | Cracauer et al. | 606/108 |
| 5,645,519 A | | 7/1997 | Lee et al. | 600/114 |
| 5,681,342 A | * | 10/1997 | Benchetrit | 606/192 |
| 5,743,851 A | | 4/1998 | Moll et al. | 600/204 |
| 5,749,357 A | * | 5/1998 | Linder | 128/200.26 |
| 5,810,790 A | | 9/1998 | Ebling et al. | 604/523 |
| 5,840,013 A | | 11/1998 | Lee et al. | 600/114 |
| 5,876,329 A | | 3/1999 | Harhen | 600/125 |
| 6,007,482 A | * | 12/1999 | Madni et al. | 600/115 |
| 6,060,454 A | | 5/2000 | Duhaylongsod | 514/26 |
| 6,214,022 B1 | | 4/2001 | Taylor et al. | 606/153 |
| 6,234,958 B1 | | 5/2001 | Snoke et al. | 600/114 |
| 6,277,137 B1 | | 8/2001 | Chin | 606/190 |
| 6,344,028 B1 | | 2/2002 | Barry | 604/96.01 |
| 6,461,294 B1 | * | 10/2002 | Oneda et al. | 600/116 |

* cited by examiner

US 6,793,661 B2

ENDOSCOPIC SHEATH ASSEMBLIES HAVING LONGITUDINAL EXPANSION INHIBITING MECHANISMS

CROSS-REFERENCE TO RELATED APPLICATION

This application is a continuation-in-part of pending U.S. patent application Ser. No. 10/094,406, filed Mar. 8, 2002, which is a continuation-in-part of pending U.S. patent application Ser. No. 09/702,155, filed Oct. 30, 2000 and issued as U.S. Pat. No. 6,461,294 on Oct. 8, 2002.

TECHNICAL FIELD

This invention relates generally to sheath assemblies having an inflatable member, and to methods and apparatus that inhibit longitudinal expansion of a body portion of the sheath during inflation of the inflatable member.

BACKGROUND OF THE INVENTION

The use of endoscopes for diagnostic and therapeutic purposes is widespread. For example, there are upper endoscopes for examination of the esophagus, stomach and duodenum, colonoscopes for the examination of the colon, angioscopes for vascular examination, bronchoscopes for examining the bronchi, laparoscopes for examining the peritoneal cavity, and arthroscopes for the examination of joint spaces. The following discussion applies to all of these, as well as other types of endoscopes and probes inserted into the body, such as ultrasound probes.

An endoscope for examining the bronchial tract and conducting transbronchial biopsies is a good example of the usefulness of endoscopic technology. These devices, known as flexible bronchoscopes, are widely used in diagnosing pulmonary diseases since they are capable of reaching the more distal bronchi in the bronchial tract. To properly navigate and view a bronchial area, the bronchoscope is generally structured to contain a fiber optic bundle within the elongated probe section. Alternatively, the bronchoscope may utilize other means to view the bronchial area, such as a video device positioned within the bronchoscope. In addition to providing a direct viewing capability, flexible bronchoscopes generally possess a means to remove tissue samples, or other material from the bronchial tract for biopsy or culture purposes. Tissue samples for biopsy purposes may be collected using a biopsy forceps extending from the distal end of the bronchoscope or by brushing the suspect area to capture cellular material for subsequent microscopic examination. Another commonly used technique to collect cellular material is to wash, or lavage, the suspect area. When a lavage procedure is used, a solution is injected into the bronchial passage and subsequently withdrawn by suction through the distal end of the bronchoscope to capture cellular material. Following withdrawal of the lavage fluid, the cellular material may be subjected to a cytological examination or culture.

One difficulty encountered in the use of endoscopes is continuously maintaining the endoscopic probe in a selected location within a body passage during the examination. Movement of the endoscopic probe while it is positioned within a body passage may occur for a number of reasons. For example, movement of the endoscope may occur due to an unintended bodily movement of the operator while the patient is undergoing the examination, or by an involuntary movement of the patient in response to the examination. Once the distal end of the endoscope has been dislodged from its intended location, it must be carefully repositioned before the examination may be resumed. Movement of the endoscope within a body passage is particularly pronounced during bronchoscopic examinations, since the patient must continue to breathe during the examination. Further, involuntary bronchospasmodic events within the bronchial passages may occur during the examination that will disrupt the location of the distal end of the bronchoscope. A significant additional difficulty resulting from unintended patient movement may arise when a biopsy procedure is conducted. Since a biopsy forceps or brush is generally used, an uncontrolled or unintended cutting of tissue in the passage due to patient movement may lead to hemoptysis. Moreover, since the biopsy forceps, or brush may reach and perforate the pleura, pneumothorax may also occur.

Still another difficulty encountered in the use of endoscopes for diagnostic purposes is the inability to sealably isolate a portion of the endoscope from the remainder of the body passage during an endoscopic examination. To facilitate internal viewing of a passage, for example, the fluid occupying the cavity is generally removed by means of a suction channel in the endoscope, which may be followed by the introduction of a gas through an additional channel in the endoscope to distend the internal space. Other endoscopic applications may require that a fluid be retained within the portion of the body passage that has been sealably isolated. For example, in transbronchial diagnostic procedures such as bronchoalveolar lavage, the bronchoscope is used to gently irrigate the air spaces in a distal air passage with a solution. Isolation of the solution to the region surrounding the distal end of the bronchoscope is required so that cellular samples removed during the lavage are sufficiently localized to be of diagnostic value. In particular, when collecting samples by lavage for use in the diagnosis of infectious pulmonary diseases, the sample must not be contaminated by bacterial or other agents transported to the distal end of the probe by the unrestrained movement of the solution through the passage.

Increasingly, endoscopes are used with disposable sheaths that are positioned over the insertion tube of the endoscope to avoid the communication of disease from one patient to another. An additional advantage of the disposable sheath is that it allows the device to be used at more frequent intervals, since the need for lengthy cleaning and disinfection or sterilization procedures is largely eliminated. Generally, the sheath may be comprised of a flexible, thin, resilient elastomeric material, such as latex or other similar materials, or may be a relatively rigid, inelastic material such as PVC, thermoplastic polyesters, polycarbonate or the like. The sheath may fit over and either tightly or loosely surround a portion of the insertion tube of the endoscope so the insertion tube is at least partially isolated from contaminants. The sheath may include a viewing window at the distal end, and may include a plurality of internal channels, or lumens, through which biopsy samples or fluids may be either introduced or removed. Accordingly, an additional difficulty encountered during the use of endoscopes is maintaining the position of the viewing window on the distal end of the sheath in close engagement with the distal end of the insertion tube to avoid reflections which may inhibit the operator's view through the viewing window.

SUMMARY OF THE INVENTION

The invention is directed toward sheath assemblies having an inflatable member, and to methods and apparatus that inhibit longitudinal expansion of a body portion of the sheath during inflation of the inflatable member. In one aspect, a sheath assembly includes a body portion adapted to encapsulate a distal end of an insertion tube, and an inflatable member coupled to the body portion and adapted to be inflated radially outwardly from the body portion. The sheath assembly further includes an expansion-inhibiting mechanism coupled to at least one of the inflatable member and the body portion. The expansion-inhibiting mechanism advantageously inhibits a longitudinal expansion of the body portion during inflation of the inflatable member.

The expansion-inhibiting mechanism may assume a variety of alternate aspects. For example, the expansion-inhibiting mechanism may be a non-compliant member, a non-compliant sleeve member extending between first and second longitudinal positions, and a non-compliant portion of a working channel. In further aspects, the expansion-inhibiting mechanism may be a non-compliant portion of the body portion, a longitudinally-stretched portion of the body portion, and a longitudinally-stretched portion of the body portion including at least one reinforcing spring member. In still other aspects, the expansion-inhibiting mechanism may include a pressure relief device fluidly coupled to the inflatable member, or a detent mechanism disposed between the inflatable member and the enclosed distal end and adapted to engage a second detent mechanism on the insertion tube.

DETAILED DESCRIPTION OF THE INVENTION

Figure 1:
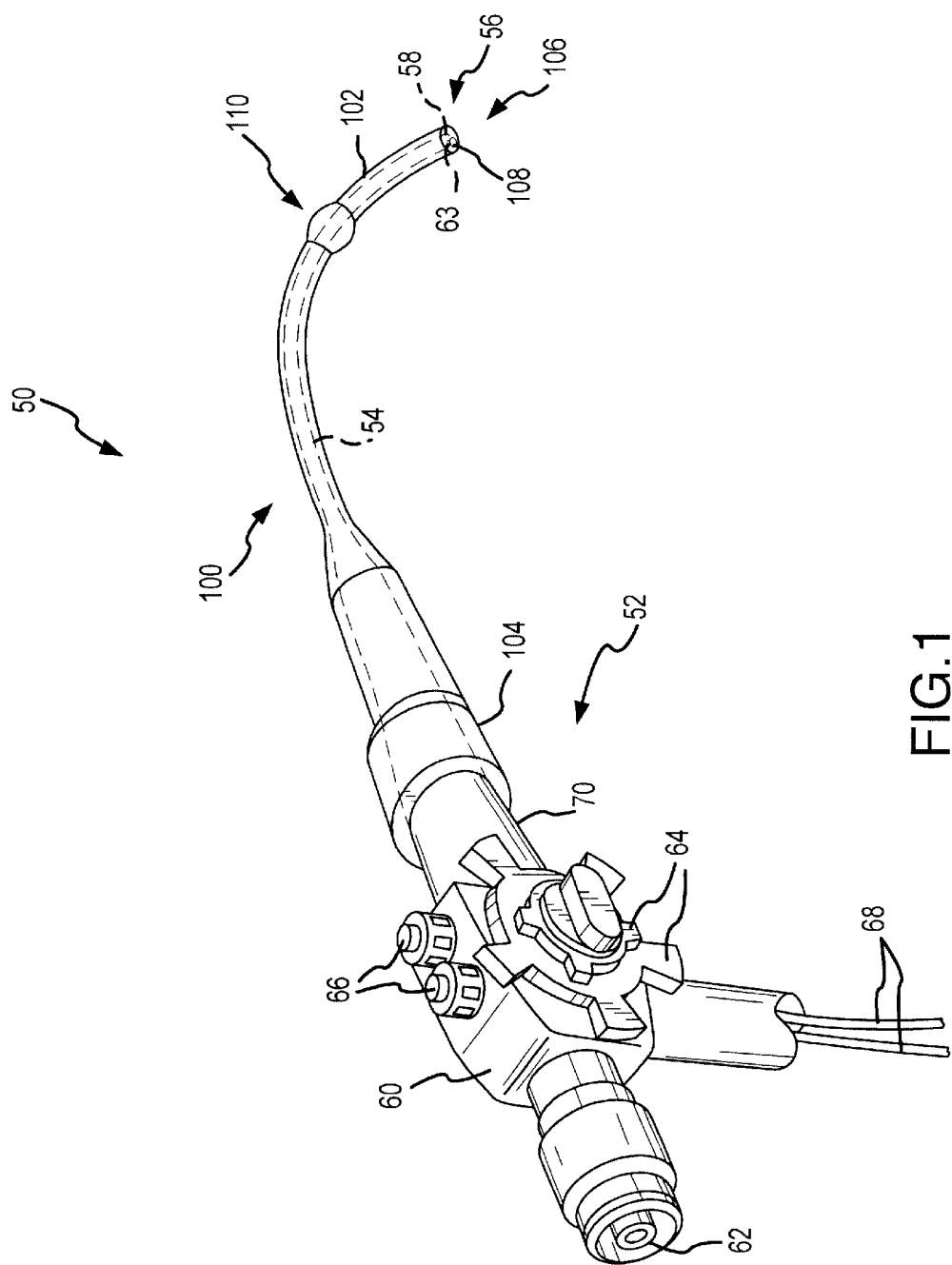
FIG. 1 is an isometric view of an endoscope assembly with an inflatable member in accordance with an embodiment of the invention.

The present invention is generally directed to sheath assemblies having inflatable members, and to methods and apparatus that provide improved operational characteristics thereof. Many of the specific details of certain embodiments of the invention are set forth in the following description and in FIGS. 1 through 18 to provide a thorough understanding of such embodiments. One skilled in the art will understand, however, that the present invention may have additional embodiments, or that the present invention may be practiced without several of the details described in the following description.

In the drawings, like reference numbers identify similar elements or steps. Further, it is understood that the inflatable members depicted in the figures may assume a variety of sizes and shapes that depend on the amount of internal pressurization and/or the internal shape of a body cavity. Accordingly, for clarity of illustration, and to properly illustrate internal features of the various embodiments illustrated in the figures, the various embodiments may not be drawn to scale and may depict various stages of inflation or operation of the inventive apparatus.

FIG. 1 is an isometric view of an endoscope assembly 50 in accordance with one embodiment of the invention. The endoscope assembly 50 includes an endoscope 52 having an elongated insertion tube 54. In this embodiment, the insertion tube 54 is flexible so that the tube may be maneuvered as it is positioned within a patient's body. Alternately, the insertion tube 54 may be rigid, partially flexible or entirely flexible. The insertion tube 54 includes a distal portion 56 having a working end 58 that is adapted to be inserted into a body cavity of a patient (not shown). The endoscope 52 shown in FIG. 1 further includes a headpiece 60 that remains external to the patient during an endoscopic procedure. The headpiece 60 includes an eyepiece 62 for viewing through a viewing aperture 63 located at the working end 58 of the insertion tube 54, a pair of bending control knobs 64 for manipulating the position of the working end 58 of the insertion tube 54, and a pair of fluid control actuators 66 for controlling the flow of gases, liquids, or vacuum through flow tubes 68 to (or from) the insertion tube 54. Endoscopes 52 of the type generally shown in FIG. 1 are described more fully, for example, in U.S. Pat. No. 5,931,833 to Silverstein, U.S. Pat. No. 5,483,951 to Frassica and Ailinger, and U.S. Pat. No. 4,714,075 to Krauter and Vivenzio, which patents are incorporated herein by reference.

As further shown in FIG. 1, the endoscope assembly 50 includes a sheath (or sheath assembly) 100 that is installed onto the insertion tube 54 of the endoscope 52. The sheath 100 includes a body portion 102 that encapsulates the insertion tube 52, and an enlarged open end (or engagement cuff) 104 that engages onto an engagement portion 70 of the endoscope 52. An enclosed distal end 106 of the sheath 100 encapsulates the working end 56 of the insertion tube 54 and includes a transparent portion (or window) 108 that is positioned proximate the viewing aperture 63. The transparent portion 108 may be integrally formed with the body portion 102 of the sheath 100, or alternately, can be a separate piece of transparent (or partially transparent) material that is fabricated separately and then attached or otherwise incorporated into the enclosed distal end 106 of the sheath 100. Preferably, the transparent portion 108 is closely engaged against the viewing aperture 63 so that undesirable reflections or glare that obscure the operator's view through the viewing aperture 63 are minimized or eliminated. As described more fully below, an inflatable member 110 is coupled to the body portion 102 of the sheath 100.

Figure 2:
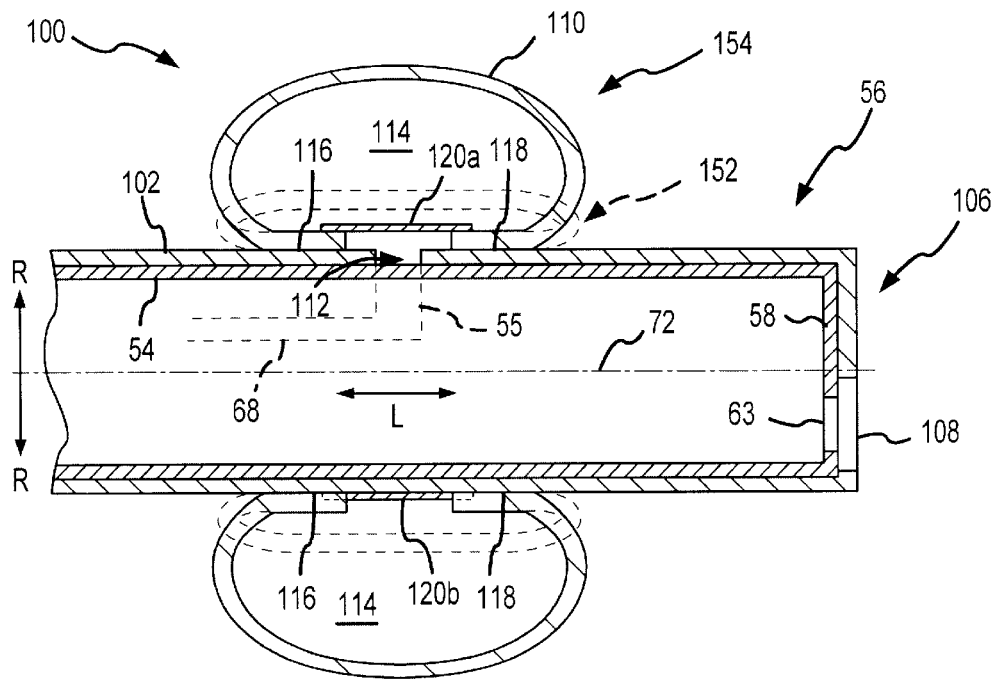
FIG. 2 is a partial cross-sectional side view of a sheath and an insertion tube of the endoscope assembly of FIG. 1.

FIG. 2 is a partial cross-sectional side view of the endoscope assembly 50 of FIG. 1. As shown in FIG. 2, the body portion 102 of the sheath 100 has an inflation port 112 therethrough that leads into an inner chamber 114 of the inflatable member 110. The inflation port 112 is coupled to one of the flow tubes 68 (FIG. 1) that extends along a longitudinal axis 72 within the sheath 100 to a pressure source (not shown). In alternate embodiments, the flow tube 68 may extend along an outer surface of the sheath 100.

As further shown in FIG. 2, the inflatable member 110 is coupled to the body portion 102 at a first position 116 and at a second position 118, and one or more non-compliant cords 120 are coupled to either the inflatable member 110 or the body portion 102, or both, proximate the first and second positions 116, 118. In this embodiment, the inflatable member 110 is circumferentially disposed about the body portion 102, and the non-compliant cords 120 are circumferentially disposed about the body portion 102 and extend longitudinally between the first and second circumferential positions 116, 118. As depicted in FIG. 2, one of the non-compliant cords 120a is coupled only to the inflatable member 110, while another one of the non-compliant cords 120b is fixed in the bond joints between the inflatable member 110 and the body portion 102.

The inflatable member 110 may be formed of any suitable material that permits the inflatable member 110 to be inflated and deflated as needed, including, for example, latex, polyurethane, KRATON®, C-FLEX®, although other suitable elastomeric materials are also acceptable. In a particular embodiment, the inflatable member 110 may be formed from a flexible and resilient material, with a durometer value of between approximately 30 and approximately 50. Alternatively, the inflatable member 110 may be formed from a relatively inelastic material so that it exhibits a relatively baggy shape when not inflated. The wall thickness of the inflatable member 110 may be any suitable thickness. In one particular aspect, for example, the wall thickness falls within the range between 0.003 and 0.010 inches, inclusive.

Conversely, the non-compliant cords 120 are formed from any suitable relatively-inelastic material so that the non-compliant cords 120 are not appreciably stretched by the inflation of the inflatable member 110. Suitable materials for the non-compliant cord 120 include, but are not limited to, any conventional high-strength polymeric materials such as polyethylene terephthalate (PET), nylon, polyethylene, polyurethane, fluoropolymers, or even non-polymeric materials such as glass strands, metallic wires, or natural-fiber cord materials that do not appreciably stretch under the loads usually encountered during normal inflation of the inflatable member 110.

In operation, a pressurized liquid or gas (e.g. air or an inert gas) may be pumped into the interior of the sheath 100 between the body portion 102 and the insertion tube 54, and through the inflation port 112 into the chamber 114, causing the inflatable member 110 to expand from a first, non-inflated (or deflated) position 152 to a second, inflated position 154. Alternately, as shown in FIG. 2, a flow tube 68 may extend along the outer surface of the insertion tube 54 between the insertion tube 54 and the body portion 102, and may be coupled to the inflation port 116 to permit the inflatable member 110 by pumping a pressurized liquid or gas through the flow tube 68. In yet another alternate embodiment, the flow tube 68 may extend along the interior of the insertion tube 54 and may be coupled to the inflation port 116 through an exhaust port 55 disposed through the insertion tube 54.

The inflatable member 110 expands outwardly in a radial direction R until the inflation member 110 engages against the surrounding walls of the patient's body cavity (or until the pressure source is shut off). In the inflated position, the inflatable member 110 may be used to fix the position of the distal portion 56 of the insertion tube 54 within the body cavity, to create a space between adjacent organs in a body cavity, or to fluidly isolate a portion of the body cavity so that lavage or any other type of medical procedure may be successfully conducted. Because the non-compliant cords 120 do not appreciably stretch in a longitudinal direction L during the inflation of the inflatable member 110, the first and second positions 116, 118 do not move farther apart along the longitudinal axis 72 of the insertion tube 54, and the longitudinal expansion of the inflatable member 110 is substantially inhibited or eliminated.

The sheath 100 having the inflatable member 110 and including the non-compliant members 120 may provide significant operational advantages over alternate sheath embodiments having inflation members. Because the longitudinal expansion of the inflatable member 110 is substantially inhibited or eliminated, the enclosed distal end 106 of the sheath 100 is more likely to remain proximate to, or closely engaged with, the working end 58 of the insertion tube 54. Consequently, the transparent portion (or window) 108 of the sheath 100 is more likely to remain aligned with, and proximate to, the viewing aperture 63, thereby reducing the possibility of spurious reflections and glare, and maintaining or improving the operator's view through the viewing aperture 63 during the medical procedure.

Figure 17:
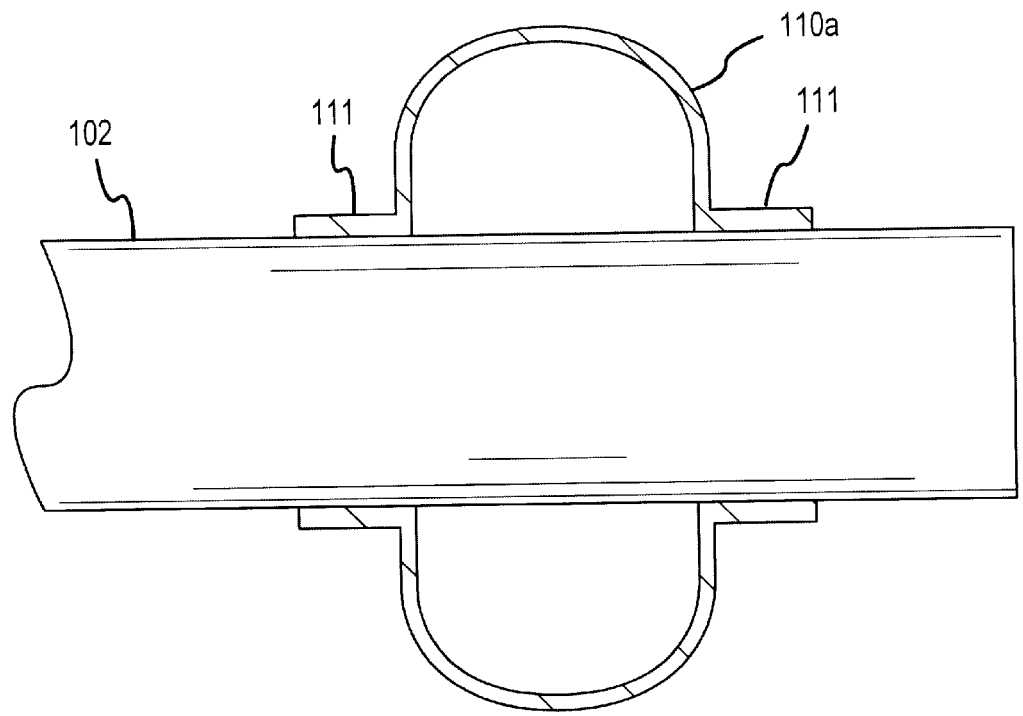
FIG. 17 is a partial cross-sectional schematic representation of an assembly in accordance with an alternate embodiment of the invention.
Figure 18:
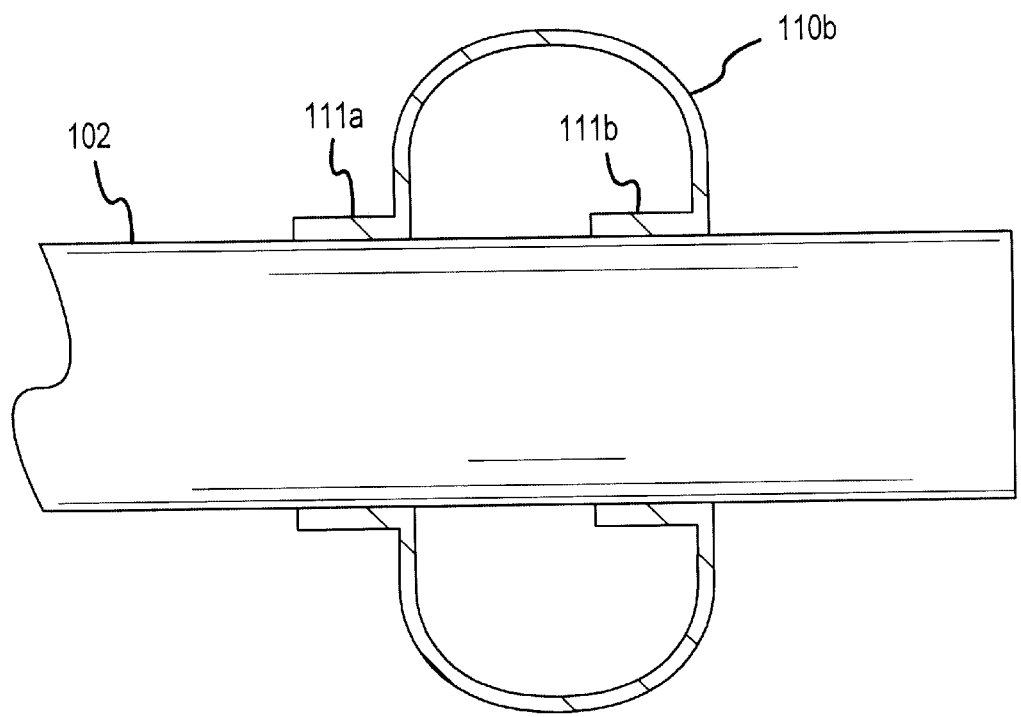
FIG. 18 is a partial cross-sectional schematic representation of an assembly in accordance with another alternate embodiment of the invention.

One may note that the inflatable member 110 may be attached to the surface of the body portion 102 of the sheath 100 in a variety of alternate configurations and using a variety of alternate attachment methods, such as, for example, by using suitable adhesives, or by thermally fusing the inflatable member 110 to the body portion 102, or by wrapping lengths of a retaining cord over the edges of the inflatable member 110. Such alternate configurations and attachment methods have been shown and described in greater detail in commonly owned U.S. patent application Ser. No. 10/094,406, incorporated herein by reference. For example, FIGS. 17 and 18 show simplified, partial cross-sectional representations of assemblies having alternate methods of attaching the inflatable member 110 to the body portion 102. Specifically, in FIG. 17, the ends 111 of the inflatable member 110a extend longitudinally along the body portion 102 rather than being inverted prior to attachment as depicted in FIG. 2. Similarly, in FIG. 18, a first end 111a of the inflatable member 110b is coupled to the body portion 102 in a longitudinally-extended manner, and the second end 111b of the inflatable member 110b is coupled to the body portion 102 in an inverted manner. These and other methods of forming and attaching the inflatable member 110 on the body portion 102 of the sheath are shown and described in greater detail in the above-referenced co-pending, commonly owned patent application.

Furthermore, it should be understood that the inflatable member 110 may be symmetrically or asymmetrically disposed about the insertion tube 54. For example, as taught in FIG. 15 of the above-referenced U.S. patent application Ser. No. 10/094,406, in alternate embodiments, the inflatable member 110 may assume any desired shape, including, for example, an eccentrically-disposed circular shape, or a non-circular, asymmetric shape, or any other suitable shape. Similarly, the insertion tube 54 can have a variety of cross sectional shapes, such as circular, semicircular, or any other desired shape. It should be further noted that the sheath 100 may include a plurality of inflatable members located anywhere along the length of the sheath 100.

Several alternate embodiments of endoscope assemblies in accordance with the invention will be described below. Generally, in the following discussion, where the construction and operation of alternate embodiments is substantially similar to previously described embodiments, the common elements and features are identified by reference numbers which are the same or similar to those used above. For the sake of brevity, only significant differences in construction or operation are described in detail.

Figure 3:
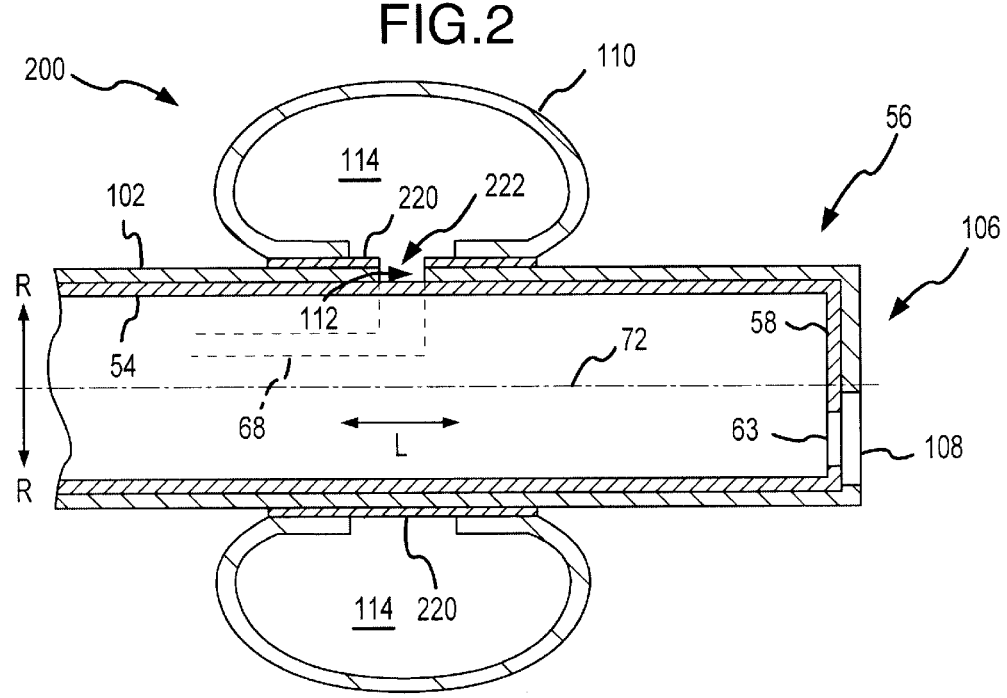
FIG. 3 is a partial cross-sectional side view of a sheath and an insertion tube of an endoscope assembly in accordance with an alternate embodiment of the invention.

FIG. 3 is a partial cross-sectional side view of a sheath 200 and an insertion tube 54 of an endoscope assembly 250 in accordance with an alternate embodiment of the invention. In this embodiment, the sheath 200 includes a non-compliant, partially tubular sleeve 220. The non-compliant sleeve 220 is disposed about the body portion 102 of the sheath 200 proximate the inflation port 112, and has an inlet port 222 aligned with the inflation port 112 to permit inflation of the inflatable member 110. As shown in FIG. 3, in this embodiment, the non-compliant sleeve 220 is attached to the body portion 102 and the inflatable member 110 is attached to the non-compliant sleeve 220. In an alternate embodiment, the non-compliant sleeve 220 may have a shorter longitudinal length so that the inflatable member 110 attaches to both the body portion 102 and the non-compliant sleeve 220.

As described above with respect to the previously described embodiment, the sheath 200 including the non-compliant sleeve 220 as shown in FIG. 3 advantageously reduces or eliminates the longitudinal expansion of the inflatable member 110 during inflation. Consequently, the transparent portion (or window) 108 of the sheath 200 is more likely to remain properly positioned with respect to the viewing aperture 63, thereby reducing spurious reflections and maintaining or improving the operator's view through the viewing aperture 63 during a medical procedure.

Figure 4:
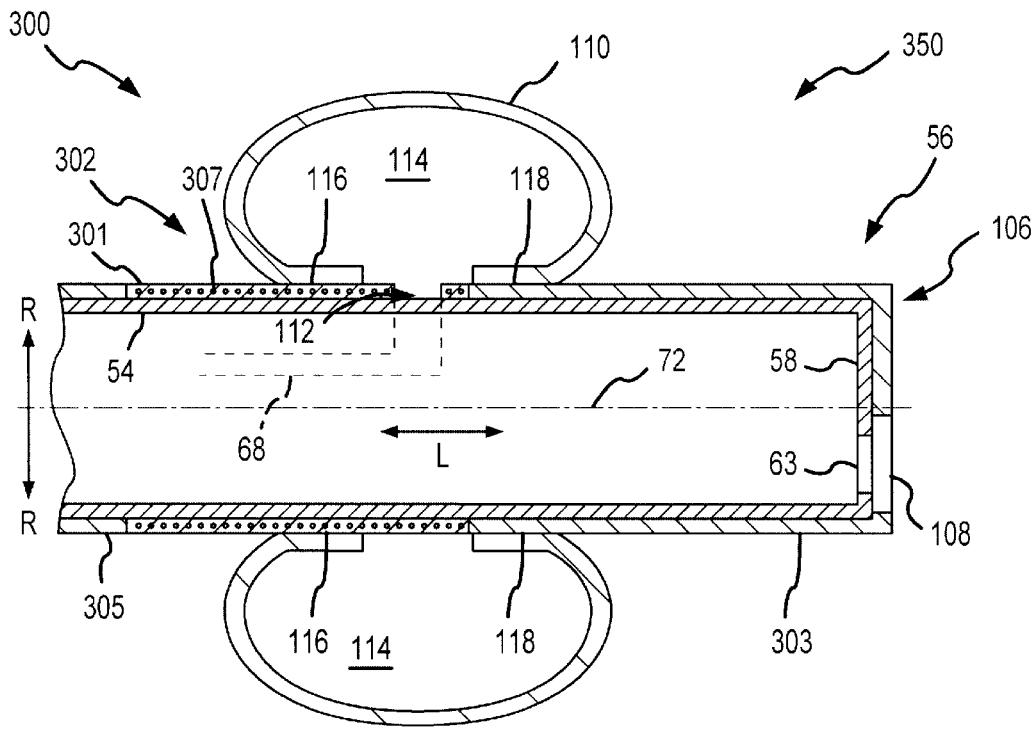
FIG. 4 is a partial cross-sectional side view of a sheath and an insertion tube of an endoscope assembly in accordance with another embodiment of the invention.

FIG. 4 is a partial cross-sectional side view of a sheath 300 and an insertion tube 54 of an endoscope assembly 350 in accordance with another embodiment of the invention. In this embodiment, the sheath 300 includes a body portion 302 having a first, radially non-compliant portion 301, and a second, radially compliant portion 303 encapsulating the distal end 56 of the insertion tube 54 and the second position 118. As shown in FIG. 4, the radially non-compliant portion 301 may include one or more reinforcing spring members 307. One may note that the first portion 301 may be both radially and longitudinally non-compliant, or even radially non-compliant and longitudinally compliant. Similarly, the second portion 303 may be both radially and longitudinally compliant, or radially compliant and longitudinally non-compliant.

In the embodiment shown in FIG. 4, the body portion 302 further includes a third, proximal compliant portion 305 between the first, radially non-compliant portion 301 and the open end 104 (FIG. 1) of the sheath 300. The inflatable member 110 is attached to the radially non-compliant portion 301 at the first attachment location 116, and to the radially compliant portion 303 at the second attachment location 118.

In operation, a pressurized liquid or gas (e.g. air or an inert gas) may be pumped through the inflation port 112 into the chamber 114, causing the inflatable member 110 to expand. As it inflates, the inflatable member 110 expands outwardly in a radial direction R, however, because it is attached to the radially compliant portion 303 of the body portion 302, the body portion 102 proximate to the second position 118 moves radially inwardly, becoming tightly engaged (or clamped) against the insertion tube 54, thereby preventing the body portion 102 proximate to the second position 118 from moving in the longitudinal direction L along the longitudinal axis 72 of the insertion tube 54. On the other hand, since the first position 116 is attached to the non-radially compliant portion 301, the body portion 102 proximate to the first position 116 does not move radially inwardly during inflation of the inflatable member 110, thereby allowing the body portion 102 proximate the first attachment position 116 to remain unclamped (or loosely engaged with the insertion tube 54), permitting the body portion 102 proximate the first attachment position 116 to slide longitudinally along the insertion tube 54.

Since the second position 118 does not move in the longitudinal direction L, the longitudinal expansion of the inflatable member 110 is restricted to move only in the proximal direction (i.e. toward the headpiece 60 or the open end 104 of the sheath 100). Thus, as described more fully above, the sheath 300 including the radially compliant portion 303 attached to the inflatable member 110 advantageously restricts longitudinal movement of the body portion 102 proximate to the second position 118, including some or all of the radially compliant portion 303. This advantageously causes the transparent portion 108 of the sheath 300 to be more likely to remain properly positioned with respect to the viewing aperture 63, thereby maintaining or improving the operator's view through the viewing aperture 63 during a medical procedure.

Figure 5:
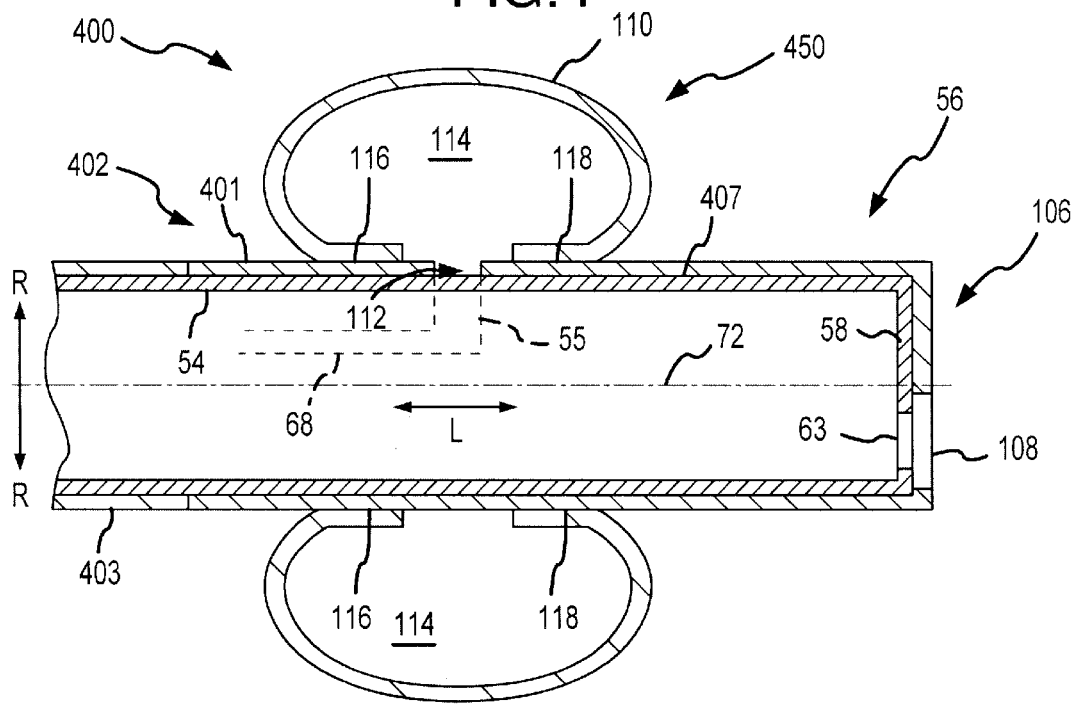
FIG. 5 is a partial cross-sectional side view of a sheath and an insertion tube of an endoscope assembly in accordance with yet another embodiment of the invention.

FIG. 5 is a partial cross-sectional side view of a sheath 400 and an insertion tube 54 of an endoscope assembly 450 in accordance with yet another embodiment of the invention. In this embodiment, the sheath 400 includes a body portion 402 having a first, pre-loaded (or longitudinally stretched) portion 401 encapsulating the distal end 56 of the insertion tube 54, and a second, proximal non-loaded portion 403 between the pre-loaded portion 401 and the open end 104 (FIG. 1) of the sheath 400. Alternately, both the first and second portions 401, 403 may be pre-loaded. The inflation member 110 is attached at first and second longitudinal positions 116, 118 to the pre-loaded portion 401.

One may note that the desired pre-loading of the pre-loaded portion 401 may be achieved in a variety of ways, including, for example, by fabricating the sheath 400 such that the relaxed length of the body portion 402 is less than the length of the insertion tube 54 so that the body portion 402 is axially stretched when the sheath 400 is installed on the endoscope 52, as taught by U.S. Pat. No. 6,350,231 issued to Ailinger and Martone and assigned to Vision Sciences, Inc. In a further aspect, it may be desirable to add a plurality of spring members 307 (as shown in FIG. 4) between the pre-loaded portion 401 and the insertion tube 54, or embedded within the pre-loaded portion 401, to prevent the pre-loaded portion 401 from collapsing down onto the insertion tube 54, particularly when subjected to an inwardly directed force from the inflation of the inflatable member 110. In yet another aspect, it may also be desirable to apply a lubricant along at least part of a contact interface 407 between the pre-loaded portion 401 and the insertion tube 54 to allow the pre-loaded portion 401 to slide longitudinally on the outer surface of the insertion tube 54. These additional aspects may advantageously help to ensure that the pre-loading (or stretching) of the pre-loaded portion 401 will overcome the tendency of the inflatable member 110 to lengthen, thus preventing the transparent portion 108 from moving away from the viewing aperture 63.

In operation, the sheath 400 including the pre-loaded portion 401 advantageously allows the inflatable member 110 to expand radially outwardly, however, the longitudinal expansion of the inflatable member 110 does not increase as the inflatable member 110 is inflated. Because the pre-loaded portion 401 of the sheath 400 is already stretched onto the distal end 56 of the insertion tube 54, the first and second positions 116, 118 are already stretched apart in the longitudinal direction L, and therefore, do not move farther apart in the longitudinal direction L. Thus, the transparent portion 108 of the sheath 400 is more likely to remain properly positioned with respect to the viewing aperture 63 during a medical procedure.

Figure 6:
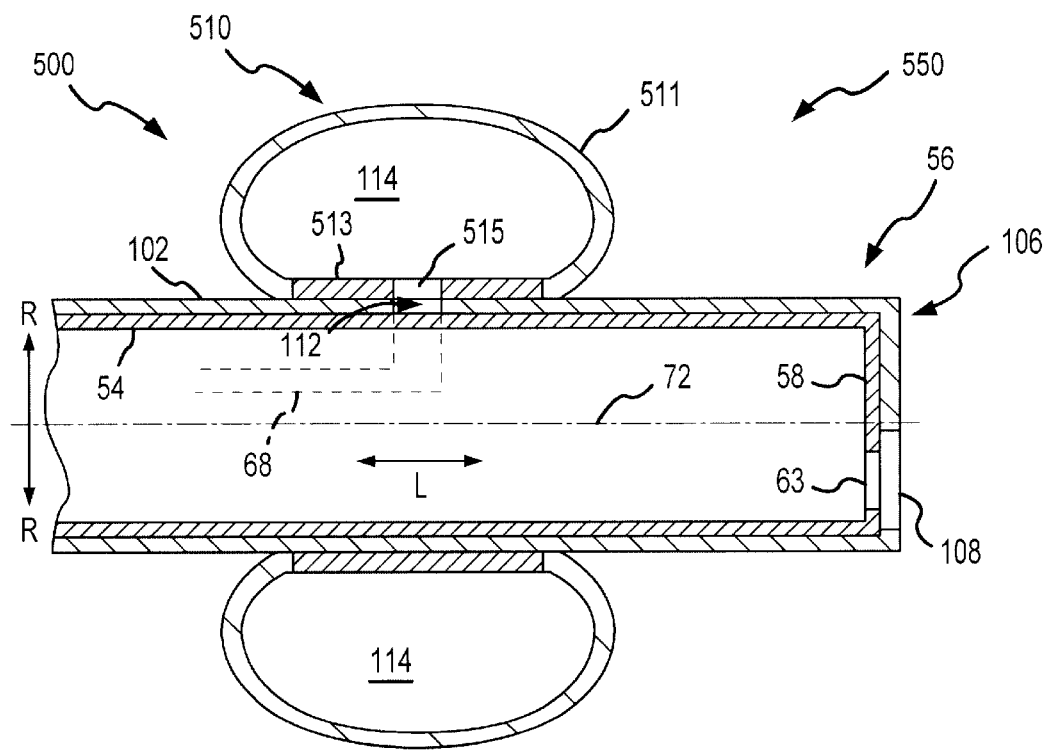
FIG. 6 is a partial cross-sectional side view of a sheath and an insertion tube of an endoscope assembly in accordance with still another embodiment of the invention.

FIG. 6 is a partial cross-sectional side view of a sheath 500 and an insertion tube 54 of an endoscope assembly 550 in accordance with still another embodiment of the invention. In this embodiment, the sheath 500 includes an inflatable member 510 having a first, compliant portion 511, and a second, non-compliant portion 513 attached to the body portion 102. The non-compliant portion 513 has an inlet aperture 515 disposed therethrough and aligned with the inflation port 112 of the body portion 102 of the sheath 500. Alternately, the first portion 511 and the second portion 513 could both be non-compliant.

In operation, as the inflatable member 510 is inflated, the compliant portion 511 expands outwardly in the radial direction R, however, the non-compliant portion 513 inhibits or prevents the inflatable member 510 from expanding longitudinally. Consequently, during inflation, the inflatable member 510 does not impart a longitudinal force on the body portion 102 of the sheath 500. Thus, the sheath 500 advantageously reduces or eliminates longitudinal movement of the transparent portion 108 during inflation, thereby maintaining or improving the operator's view through the viewing aperture 63 during a medical procedure as described more fully above.

Figure 7:
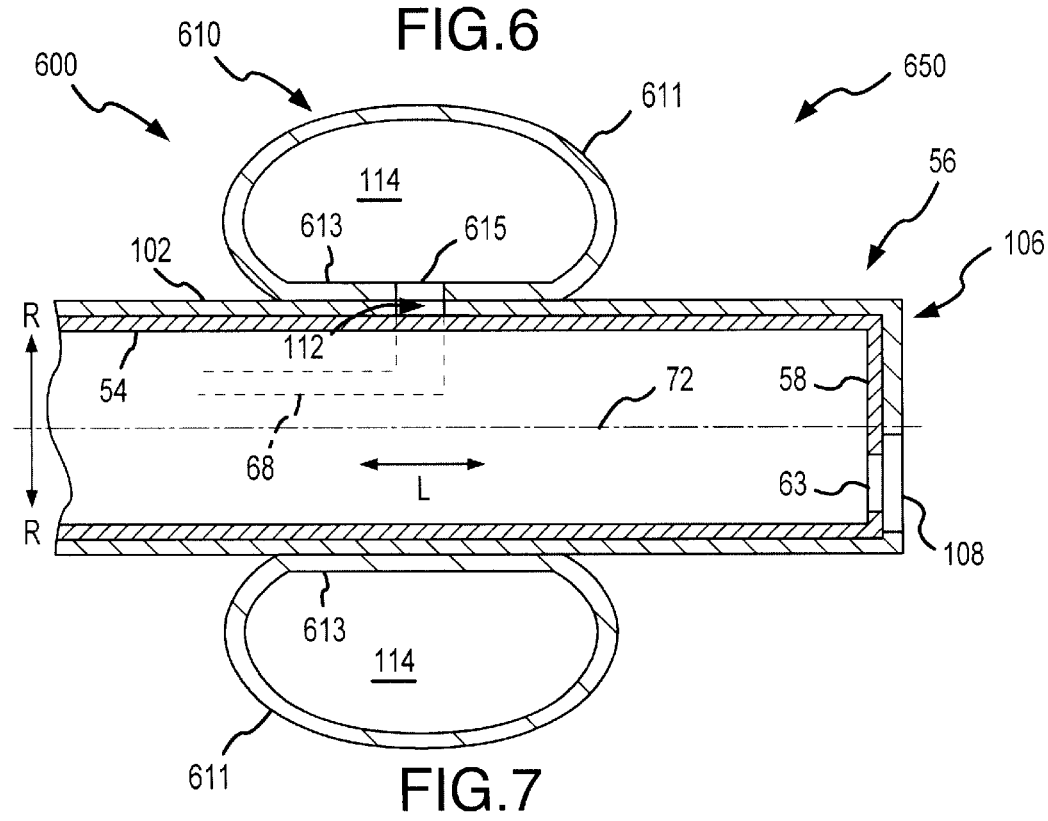
FIG. 7 is a partial cross-sectional side view of a sheath and an insertion tube of an endoscope assembly in accordance with another alternate embodiment of the invention.

FIG. 7 is a partial cross-sectional side view of a sheath 600 and an insertion tube 54 of an endoscope assembly 650 in accordance with another alternate embodiment of the invention. As shown in FIG. 7, the sheath 600 includes an inflatable member 610 that includes an outer wall 611 and a relatively-thinner inner sleeve 613 attached to the body portion 102. The inner sleeve 613 has an inlet aperture 615 disposed therethrough and aligned with the inflation portion 112. Both the outer wall 611 and the inner sleeve 613 may be formed of the same (or different) compliant material, however, the inner sleeve 613 is relatively thinner than the outer wall 611.

As the inflatable member 610 is inflated, the relatively-thinner inner sleeve 613 stretches more readily than the outer wall 611. The inflatable member 610 with the relatively-thinner inner sleeve 613 allows the pressure inside the inflatable member 610 to collapse the inner sleeve 613, and the segment of the body portion 102 that the inner sleeve 613 is attached to, to collapse tightly onto the insertion tube 54, thus locking the body portion 102 in position on the insertion tube 54 and preventing the enclosed distal end 106 of the sheath 600 from being displaced from the working end 58 of the insertion tube 54. Again, the sheath 600 advantageously reduces or eliminates longitudinal movement of the transparent portion 108, thereby maintaining or improving the operator's view through the viewing aperture 63 during a medical procedure.

Figure 8:
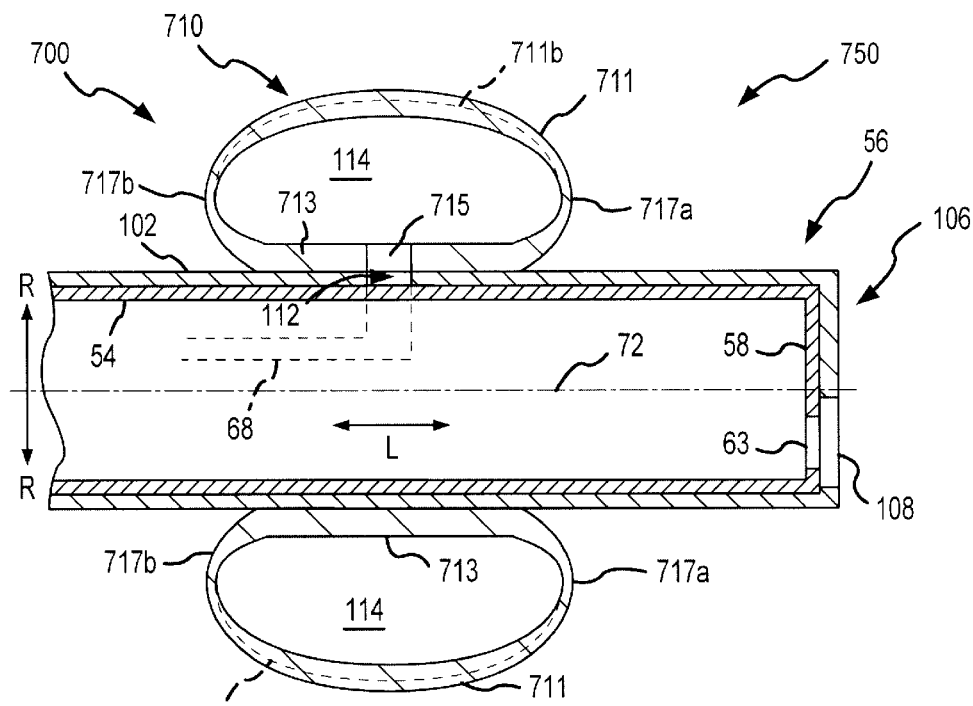
FIG. 8 is a partial cross-sectional side view of a sheath and an insertion tube of an endoscope assembly in accordance with yet another alternate embodiment of the invention.

FIG. 8 is a partial cross-sectional side view of a sheath 700 and an insertion tube 54 of an endoscope assembly 750 in accordance with yet another alternate embodiment of the invention. In this embodiment, the sheath 700 includes an inflatable member 710 having non-uniform peripheral wall thickness. Specifically, the inflatable member 710 includes a relatively-thick outer wall 711 and a relatively-thick inner wall 713 that is coupled to the body portion 102. The outer wall 711 is coupled to the inner wall 713 by relatively-thin sidewalls (or transition sections) 717 (or forward and rearward walls 717a, 717b). In the embodiment depicted in FIG. 8, the outer and inner walls 711, 713 are approximately three times thicker than the sidewalls 717, although other ratios of wall thickness are feasible. An inlet port 715 is disposed through the inner wall 715 and aligned with the inflation port 112 of the body portion 102 to permit inflation of the inflatable member 710.

One may note that both the outer and inner walls 711, 713, and the sidewalls 717, may be formed of the same (or different) compliant materials. Alternately, the outer and inner walls 711, 713 may be formed of a non-compliant material, and the sidewalls 717 may be formed of a compliant material, similar to the embodiment described above and shown in FIG. 6.

In operation, as the inflatable member 710 is inflated, the relatively-thinner sidewalls 717 stretch more readily than the outer and inner walls 711, 713 due to their relative thicknesses. The inflatable member 710 thereby expands readily in the radial direction R and relatively less in the longitudinal direction L. Thus, the body portion 102 of the sheath 700 has less tendency to slide along the insertion tube 54 during inflation of the inflatable member 710, and the enclosed distal end 106 of the sheath 700 remains properly positioned proximate the working end 58 of the insertion tube 54. Again, the sheath 700 advantageously reduces or eliminates longitudinal movement of the transparent portion 108, thereby maintaining or improving the operator's view through the viewing aperture 63 during a medical procedure.

With continued reference to FIG. 8, in another embodiment, the inflatable member 710 may have a relatively-thick inner wall 713, and the outer wall 711b (shown in dotted lines in FIG. 8) and the sidewalls 717 may be relatively thinner than the inner wall 713. As the inflatable member 710 is inflated, the relatively-thinner sidewalls 717 and outer wall 713b stretch more readily than the inner wall 711, thereby allowing the inflatable member 710 to readily expand in the radial direction R and inhibiting expansion in the longitudinal direction L.

Figure 9:
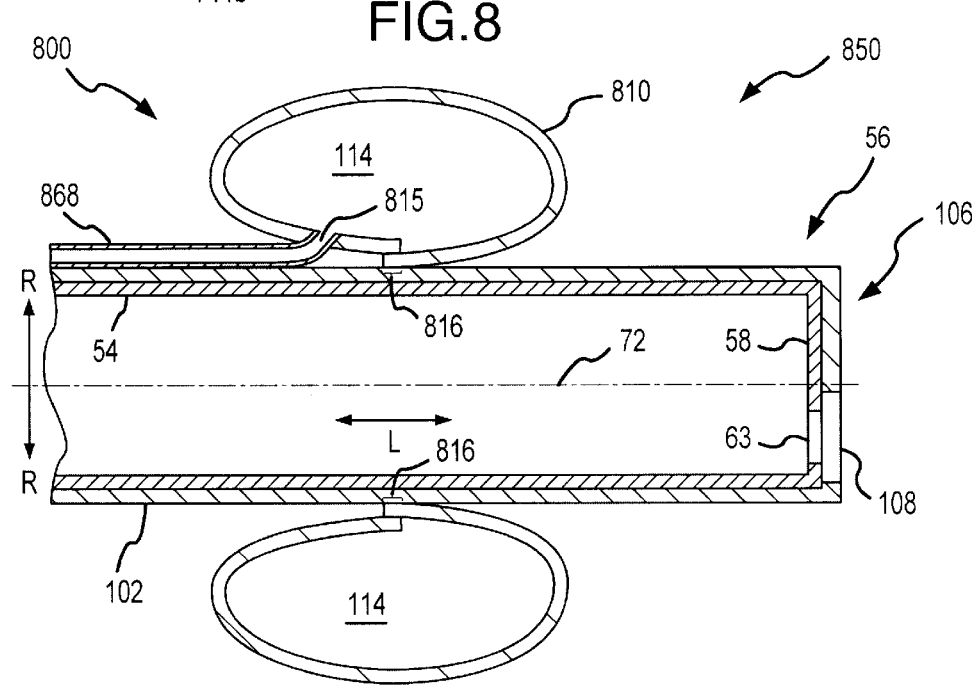
FIG. 9 is a partial cross-sectional side view of a sheath and an insertion tube of an endoscope assembly in accordance with still another alternate embodiment of the invention.

FIG. 9 is a partial cross-sectional side view of a sheath 800 and an insertion tube 54 of an endoscope assembly 850 in accordance with still another embodiment of the invention. In this embodiment, the sheath 800 includes an inflatable member 810 that is attached to the body portion 102 along a relatively-narrow attachment band 816. A flow tube 868 extends along an outer surface of the body portion 102 and is coupled to an inlet port 815 to permit inflation of the inflatable member 810.

It should be understood that FIG. 9 is not drawn to scale, and that the actual longitudinal extent of the attachment band 816 may be varied from the particular embodiment shown in FIG. 9. For example, in a particular embodiment, the ratio of the longitudinal extent of the attachment band 816 to the overall longitudinal extent of the inflatable member 810 in the deflated position may be less than or equal to 20%. Alternately, in other embodiments, the ratio may be less than or equal to 10%, and in further embodiments, the ratio may be less than or equal to 2%. The invention should not be construed as being limited to these specific embodiments, however, as any suitable extent of the attachment band 816 may be employed. Alternately, the attachment band 816 may be wide enough to allow for inflation from inside the sheath while still being narrow enough to limit elongation.

In operation, a gas or liquid from a pressure source is pumped through the flow tube 868 and into the chamber 114 to inflate the inflatable member 810. Because the inflatable member 810 is attached to the body portion 102 along the relatively narrow attachment band 816, the expansion of the inflatable member 810 in both the radial and longitudinal directions R, L does not exert a significant longitudinal force on the body portion 102. More specifically, it is desirable that any forces exerted by the inflation of the inflatable member 810 on the body portion 102 along the longitudinal direction L are not sufficient to overcome various forces (e.g. frictional forces) that resist longitudinal movement of the body portion 102 with respect to the insertion tube 54. Although in some embodiments, the inflation of the inflatable member 810 may still exert a small longitudinal force on the body portion 102, the inventive assembly 850 advantageously prevents significant longitudinal forces from being exerted which would overcome the other various forces that resist longitudinal movement of the enclosed distal end 106 and that would otherwise cause the enclosed distal end 106 to move away from the distal end 58 of the insertion tube 54. In this way, the sheath 800 advantageously allows the inflatable member 810 to be inflated without undesirably moving the enclosed distal end 106 of the sheath 800 away from its proper position proximate the working end 58 of the insertion tube 54.

Figure 10:
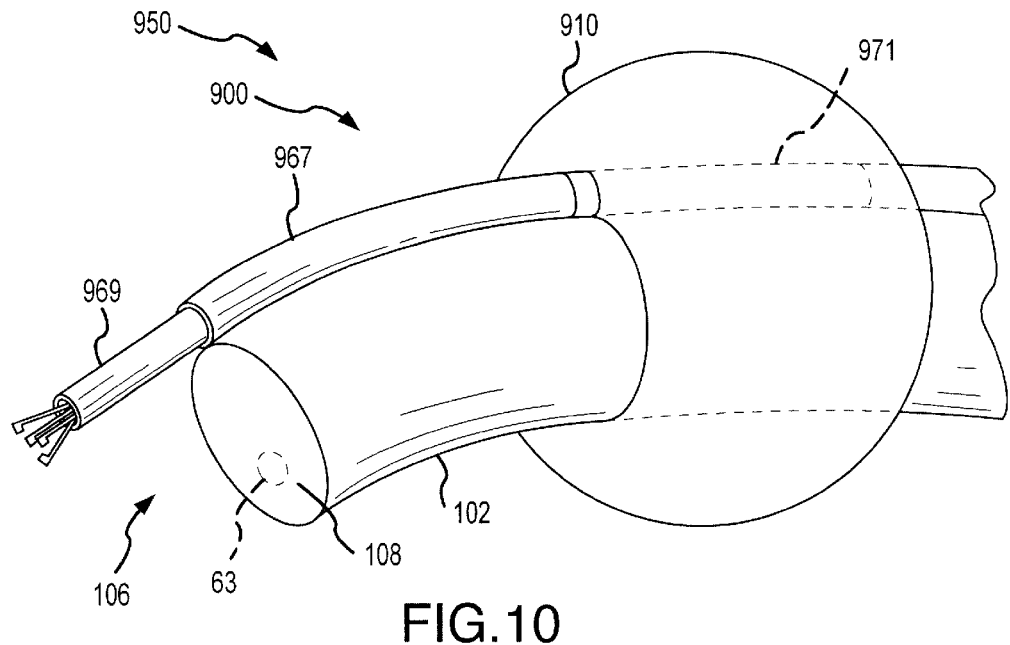
FIG. 10 is a partial isometric view of an endoscope assembly in accordance with a further embodiment of the invention.
Figure 11:
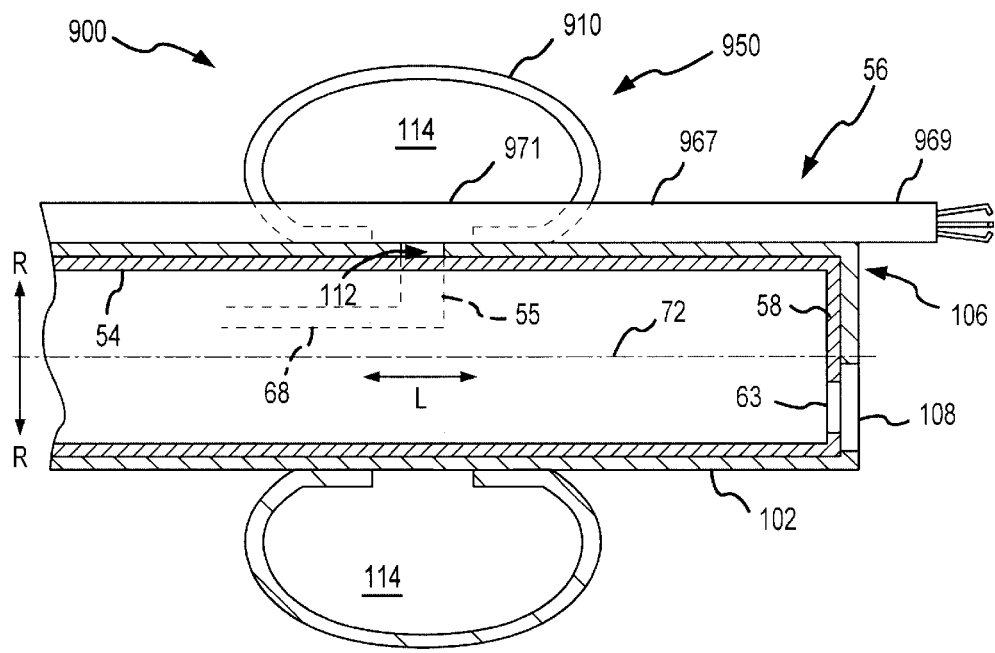
FIG. 11 is a partial cross-sectional side view of a sheath and an insertion tube of the endoscope assembly of FIG. 10.

FIGS. 10 and 11 are partial isometric and partial cross-sectional side views of an endoscope assembly 950 in accordance with a further embodiment of the invention. In this embodiment, the endoscope assembly 950 includes a sheath 900 having a channel 967 that extends longitudinally along the outer surface of the body portion 102. In alternate embodiments, the channel 967 may extend along the inner surface of the body portion 102, between the body portion 102 and the insertion tube 54. As shown in FIGS. 10 and 11, the channel 967 includes a non-compliant portion 971. An inflatable member 910 is attached to the body portion 102 and to the channel 967 proximate the non-compliant portion 971. In this embodiment, the inflatable member 910 may preferably be symmetrically disposed about the non-compliant portion 971. A medical instrument 969 may be inserted through the channel 967 and extends from the channel 967 beyond the working end 56 of the insertion tube 54. In this embodiment, the medical instrument 969 is a biopsy sampling device, although any other desired medical device may be used. The channel 967 may also be used to introduce or withdraw a fluid such as air or water, or for any other desired purpose. The chamber 114 of the inflatable member 910 fluidly communicates with the flow tube 68 within the insertion tube 54 via the inflation port 112 in the body portion 102 of the sheath 900.

One may note that in alternate embodiments, more than one channel may be added to either the outer (or inner) surface of the sheath in the, manner shown in FIGS. 10 and 11, or alternately, there could be one or more channels on the outer surface and one or more channels on the inner surface. Furthermore, the longitudinal extent of the non-compliant portion 971 of the channel 967 may be varied (increased or decreased) from the particular configuration shown in FIGS. 10 and 11, including, for example, extending the non-compliant portion 971 all the way to the working end 56 of the insertion tube 54. Preferably, the non-compliant portion 971 has a longitudinal extent that is sufficient to prevent the inflatable member 910 from clamping the compliant portions of the working channel 967 that are adjacent the non-compliant portion 971 inwardly against the medical instrument 969 during inflation of the inflation member 910, thereby inhibiting the operability of the medical instrument 969.

In operation, as the inflatable member 910 is inflated in the manner described above, the inflatable member 910 is free to expand radially outwardly away from the body portion 102. As the expanding inflatable member 910 begins to assert a longitudinal force on the body portion 102, however, the non-compliant portion 971 of the channel 967 resists the longitudinal force, substantially inhibiting or preventing the inflatable member 910 from moving the body portion 102 in the longitudinal direction L on the insertion tube 54. Consequently, the sheath 900 advantageously allows the inflatable member 910 to be inflated without undesirably moving the enclosed distal end 106 of the sheath 900 away from its proper position proximate the working end 58 of the insertion tube 54.

Figure 12:
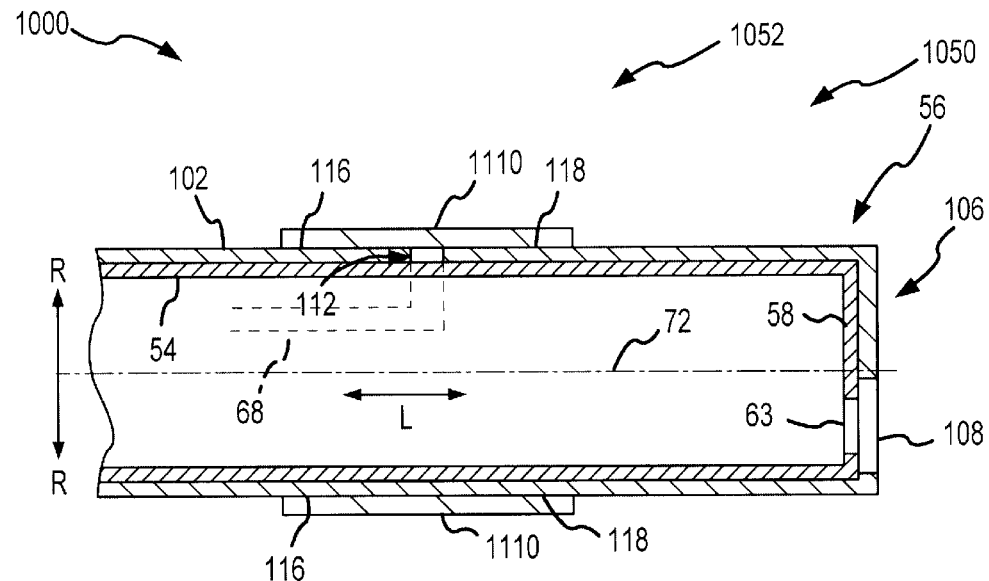
FIG. 12 is a partial cross-sectional side view of a sheath and an insertion tube of an endoscope assembly in a first operational position in accordance with another embodiment of the invention.

FIG. 12 is a partial cross-sectional side view of a sheath 1000 and an insertion tube 54 of an endoscope assembly 1050 in a first operational position 1052 in accordance with another embodiment of the invention. The sheath 1000 includes an inflatable member 1110 that, in the first (or deflated) operational position 1052, is attached in an approximately flush manner to the body portion 102 at first and second attachment regions 116, 118 on opposing sides of the inflation port 112. In one aspect, the inflatable member 1110 may be unstretched between the first and second attachment points 116, 118, however, in a preferred aspect, the inflatable member 1110 is stretched in the longitudinal direction L when the sheath 1000 is positioned onto the insertion tube 54 in the first operational position 1052.

Figure 13:
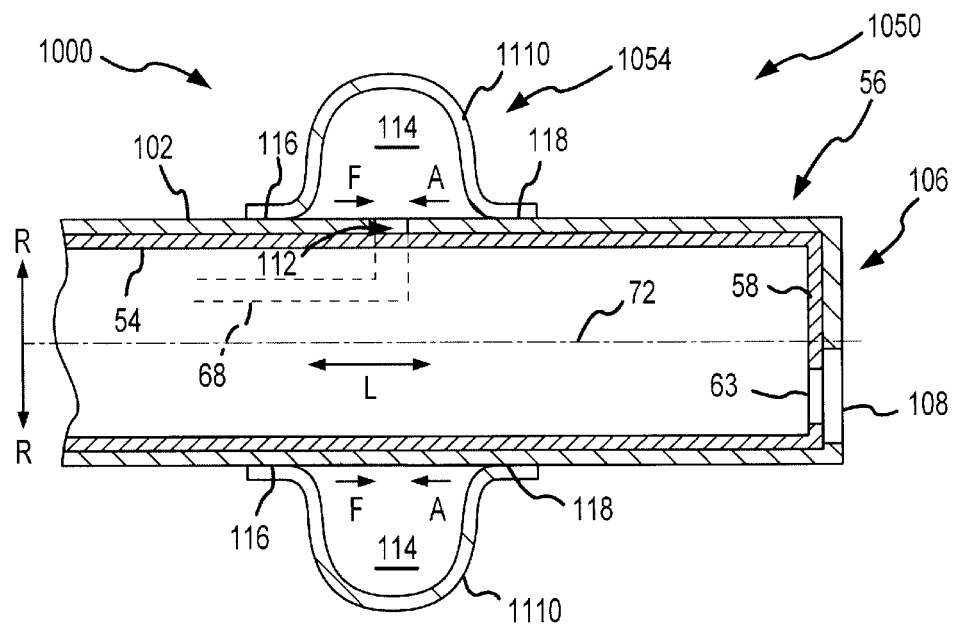
FIG. 13 is a partial cross-sectional side view of a sheath and an insertion tube of the endoscope assembly of FIG. 12 in a second operational position.

FIG. 13 is a partial cross-sectional side view of the endoscope assembly 1050 of FIG. 12 in a second (or inflated) operational position 1054. As shown in FIG. 13, in the second operational position 1054, the chamber 114 of the inflatable member 1110 is pressurized so that the inflatable member 1110 expands outwardly in the radial direction R away from the body portion 102 of the sheath 1000. As the inflatable member 1110 is inflated, the tension force in the inflatable member 1110 exerts a force on the first attachment region 116 in a forward direction F toward the working end 56 of the insertion tube 54, and also exerts a force on the second attachment region 118 in an aftward direction A away from the working end 56 of the insertion tube 54. In other words, during inflation of the inflatable member 1110, forces are exerted on the first and second attachment regions 116, 118 that tend to draw the first and second attachment regions 116, 118 toward each other. Moreover, the force exerted on the second attachment region 118 tends to draw the enclosed distal end 106 of the sheath 1000 into closer engagement with the working end 56 of the insertion tube 54.

The sheath 1000 having the inflatable member 1110 thereby inhibits or prevents the transparent portion 108 of the sheath 1000 from moving out of position with respect to the viewing port 63. Because the expansion of the inflatable member 1110 exerts a force on the body portion 102 that tends to draw the enclosed distal end 106 of the sheath 1000 more tightly onto the working end 56, the enclosed distal end 106 is more likely to remain proximate to, or closely engaged with, the working end 58 during a medical procedure. Consequently, the transparent portion (or window) 108 of the sheath 100 is more likely to remain aligned with, and proximate to, the viewing aperture 63, thereby reducing the possibility of spurious reflections and glare, and maintaining or improving the operator's view through the viewing aperture 63.

Figure 14:
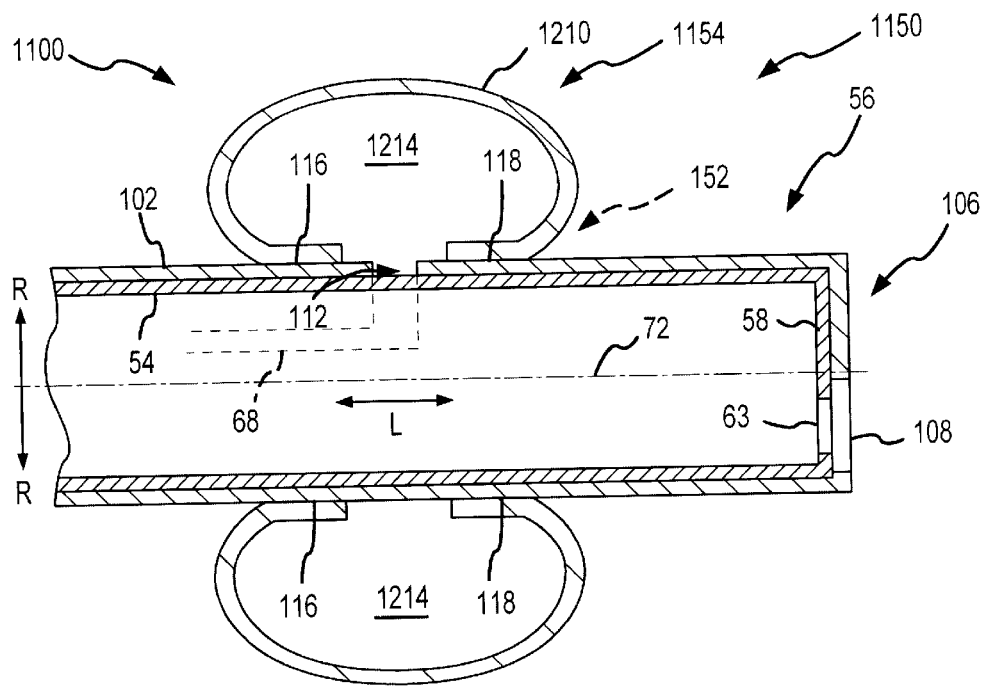
FIG. 14 is a partial cross-sectional side view of a sheath and an insertion tube of an endoscope assembly in accordance with another alternate embodiment of the invention.

FIG. 14 is a partial cross-sectional side view of a sheath 1100 and an insertion tube 54 of an endoscope assembly 1150 in accordance with another alternate embodiment of the invention. In this embodiment, the sheath 1100 includes a compliant, inflatable member 1210 having an inner chamber 1214 of a known volume. The inflatable member 1210 is attached to the body portion 102 at first and second attachment regions 116, 118.

In operation, a known volume of liquid (or gas) is pumped through the flow tube 68 into the inflatable member 1210, inflating the inflatable member 1210 from a deflated position 152 (FIG. 2) into a precisely inflated position 1154 (FIG. 14). Preferably, an approximately incompressible fluid (e.g. saline solution, water, or other liquid) is used to inflate the inflatable member 1210 so that the amount of fluid pumped into the chamber 1214 may be more accurately measured and controlled. In the precisely inflated position 1154, the inflatable member 1210 is properly inflated such that no appreciable longitudinal force is exerted by the inflatable member 1210 through the first and second attachment regions 116, 118 onto the body portion 102. Consequently, the sheath 1100 advantageously reduces or eliminates longitudinal movement of the transparent portion 108 during inflation, thereby maintaining or improving the operator's view through the viewing aperture 63 during a medical procedure.

Figure 15:
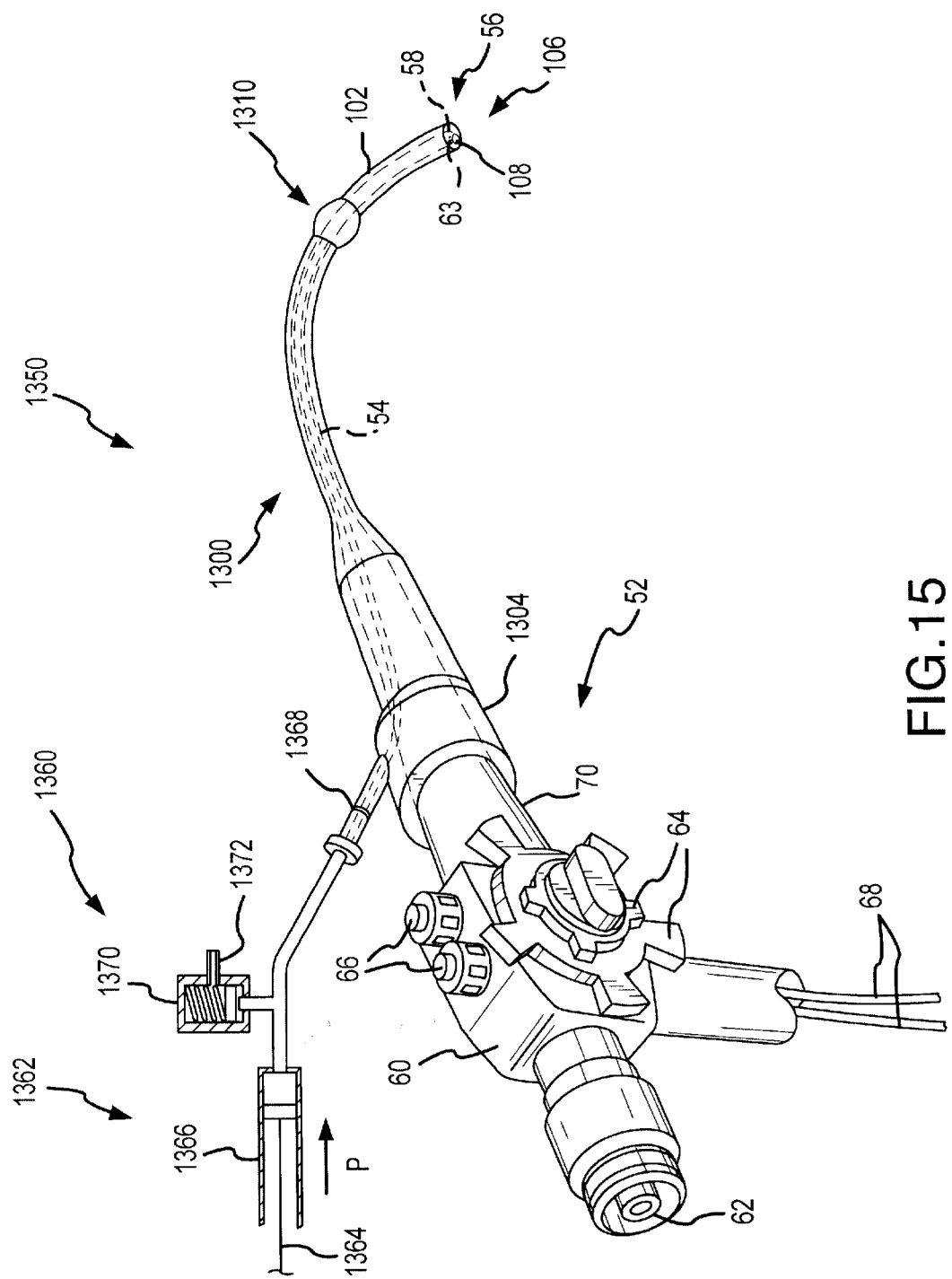
FIG. 15 is an isometric view of an endoscope assembly in accordance with yet another embodiment of the invention.

FIG. 15 is an isometric view of an endoscope assembly 1350 in accordance with yet another embodiment of the invention. The endoscope assembly 1350 includes an endoscope 52 as described above with reference to FIG. 1. As further shown in FIG. 15, the endoscope assembly 1350 includes a sheath 1300 that is installed onto the insertion tube 54 of the endoscope 52. The sheath 1300 includes a body portion 102 having an enclosed distal end 106 proximate a working end 58 of the insertion tube 54, and an inflatable member 1310 coupled to the body portion 102. An inflation system 1360 is coupled to the inflatable member 1310 via an inflation lumen 1368 that extends longitudinally along the body portion 102. In the embodiment shown in FIG. 15, the inflation lumen 1368 is disposed within the body portion 102 near the inflatable member 1310, and projects outwardly through the body portion 102 near the enlarged open end 1304 of the sheath 1300. In alternate embodiments, the inflation lumen 1362 may extend entirely along the outer surface or the inner surface of the body portion 102.

The inflation system 1360 includes an inflation source 1362 coupled to the inflation lumen 1368 that provides a flow of pressurized liquid or gas through the inflation lumen 1368 to the inflatable member 1310. In this embodiment, the inflation source 1362 includes a plunger 1364 slideably disposed within a sleeve 1366. In alternate embodiments, the inflation source 1362 may be any suitable type of device for providing the necessary flow of pressurized liquid or gas for inflation of the inflatable member 1310, including, for example, a pump, a gas bottle, or any other desired pressure source.

As further shown in FIG. 15, the inflation system 1360 also includes a pressure relief device 1370 having a vent 1372. In this embodiment, the pressure relief device 1370 is coupled to the inflation lumen 1368, however, in alternate embodiments, the pressure relief device 1370 may be coupled to the inflation source 1362, or to any other component of the inflation system 1360.

In operation, the endoscope assembly 1350 is positioned in a desired position, and the inflation source 1362 is activated to inflate the inflatable member 1310. As the inflatable member 1310 approaches the fully-inflated position, a back-pressure begins to occur within the inflation lumen 1368. In the fully-inflated position, the back-pressure reaches a predetermined level which causes the pressure relief device 1370 to release any additional pressurized liquid or gas supplied by the inflation source 1362 through the vent 1372. Thus, by proper adjustment or selection of the pressure relief device 1370, a precise amount of pressurized gas may be supplied to the inflatable member 1310 via the inflation lumen 1368.

The endoscope assembly 1350 may provide significant operational advantages. Because the amount of gas supplied to the inflatable member 1310 by the inflation source 1362 may be accurately controlled using the pressure relief device 1370, the pressure relief device 1370 may be selected or adjusted to ensure that the inflatable member 1310 is inflated in a controlled fashion to reduce or eliminate the tendency of the inflatable member 1310 to move the window 108 relative to the working end 106 of the insertion tube 54. By controlling the pressure level within the inflatable member 1310 using the pressure relief device 1370, the inflation of the inflatable member 1310 may be controlled so that the inflatable member 1310 is less likely to urge the window 108 away from the viewing aperture 63 during a medical procedure. Although in some embodiments, the inflation of the inflatable member 1310 may still exert a small longitudinal force on the body portion 102, the inventive assembly 1350 advantageously prevents significant longitudinal forces from being exerted which would overcome the other various forces that resist longitudinal movement of the enclosed distal end 106 and that would otherwise cause the enclosed distal end 106 to move away from the distal end 58 of the insertion tube 54.

Figure 16:
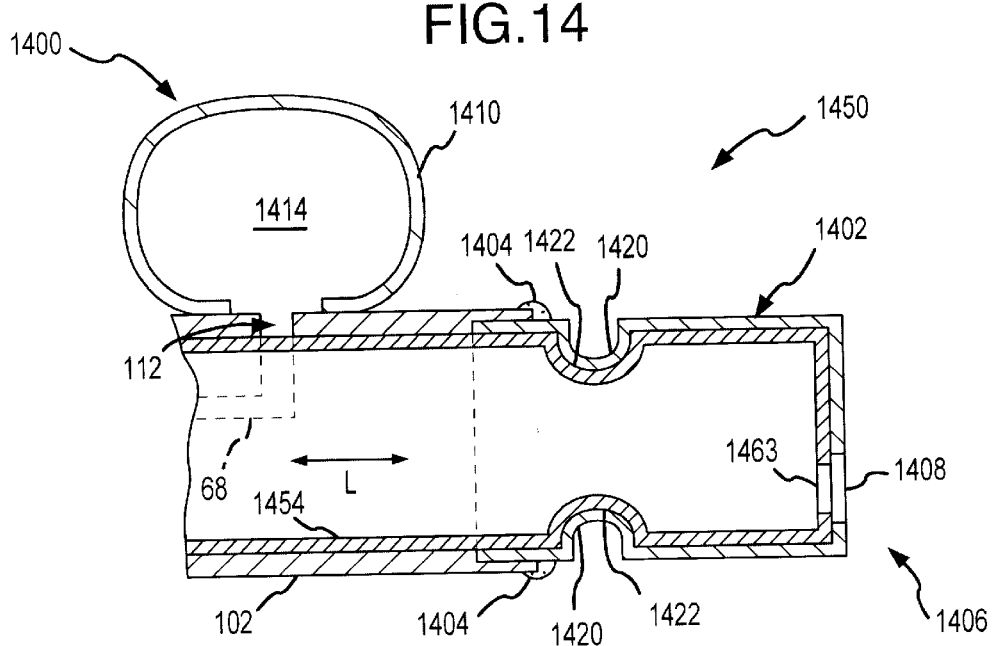
FIG. 16 is a partial cross-sectional side view of a sheath and an insertion tube of an endoscope assembly in accordance with another alternate embodiment of the invention.

FIG. 16 is a partial cross-sectional side view of a sheath 1400 and an insertion tube 1454 of an endoscope assembly 1450 in accordance with another embodiment of the invention. In this embodiment, the sheath 1400 includes a body portion 102 and a tip portion 1402 coupled to the body portion 102 at a bond region 1404 that encapsulates the working end 1406 of the insertion tube 1454. The bond region 1404 may be formed, for example, by coupling the body portion 102 to the tip portion 1402 using an adhesive material or by thermally bonding the body and tip portions 102, 1402. Alternately, the tip portion 1402 may be integrally formed with the body portion 102. The tip portion 1402 may be at least partially transparent to permit viewing through a viewing aperture 1463 disposed within the working end 1406 of the insertion tube 1454. Alternately, the tip portion 1402 may include a transparent window portion 1408 that is aligned with the viewing aperture 1463.

As further shown in FIG. 16, the tip portion 1402 includes at least one detent member 1420 that projects inwardly into one or more recesses 1422 disposed within the insertion tube 1454. In one embodiment, the detent member 1420 may be an annularly disposed, inwardly projecting ridge, and the recess may be an annular ring or groove disposed about the insertion tube 1454. Alternately, a plurality of detent members 1420 and recesses 1422 may be disposed about the circumference of the insertion tube 1454. In one aspect, for example, the detent member 1420 may be one or more partial or semi-annularly disposed, inwardly projecting ridges that engage into one or more corresponding grooves disposed about the insertion tube 1454. In another aspect, each of the recesses 1422 is a partially-spherical "dimple", and each of the detent members 1420 is a correspondingly partially-spherical bump. In further embodiments, the positions of the detent members 1420 and the recesses 1422 may be switched with the recesses 1422 disposed in the tip portion 1402 and the detent members 1420 disposed on the insertion tube 1454. In still further embodiments, the detent members 1420 and the recesses 1422 need not be confined to a single longitudinal station, but rather, may be distributed at different longitudinal positions over the surfaces of the tip portion 1402 and the insertion tube 1454, respectively.

In operation, the sheath 1400 is installed onto the insertion tube 1454 with the tip portion 1402 disposed over the working end 1406 and the detent members 1420 disposed within the recesses 1422 as shown in FIG. 16. As the inflatable member 1410 is inflated in the manner described above, the inflatable member 1410 is free to expand radially outwardly away from the body portion 102. As the expanding inflatable member 1410 begins to assert a longitudinal force on the body portion 102, however, each detent member 1420 engages with its corresponding recess 1422 to resist longitudinal movement of the tip portion 102 with respect to the working end 1406, substantially inhibiting or preventing the inflatable member 1410 from moving the body portion 102 in the longitudinal direction L with respect to the insertion tube 54. Consequently, the sheath 1400 advantageously allows the inflatable member 1410 to be inflated without undesirably moving the transparent portion 1408 of the sheath 1400 away from its proper position proximate the viewing aperture 1463 of the insertion tube 1454.

It should be noted that the disclosed methods and apparatus for inhibiting longitudinal expansion of a body portion of an endoscopic sheath during inflation of an inflatable member advantageously reduce the longitudinal expansion forces that would otherwise be exerted on the body portion during inflation of the inflatable member. Although in some embodiments, the disclosed methods and apparatus may still experience some longitudinal forces on the body portion during inflation of the inflatable member, such longitudinal forces are preferably not significant longitudinal forces which would overcome the other various forces that resist longitudinal movement that would otherwise cause the enclosed distal end of the sheath to move away from the distal end of the insertion tube. In this way, the disclosed methods and apparatus advantageously reduce or eliminate the movement of the enclosed distal end of the sheath away from its proper position proximate the working end of the insertion tube.

The above description of illustrated embodiments of the invention is not intended to be exhaustive or to limit the invention to the precise form disclosed. While specific embodiments of, and examples of, methods and apparatus for inhibiting longitudinal expansion of a body portion of an endoscopic sheath during inflation of an inflatable member in accordance with the invention are described in the foregoing for illustrative purposes, various equivalent modifications are possible within the scope of the invention, as those skilled in the relevant art will recognize. Moreover, the various embodiments described above can be combined to provide further embodiments. Accordingly, the invention is not limited by the disclosure, but instead the scope of the invention is to be determined entirely by the following claims.

What is claimed is:

1. A sheath assembly adapted for use on an insertion tube, comprising:
    a body portion adapted to at least partially encapsulate the insertion tube, the body portion having a radially non-compliant portion and a radially compliant portion; and
    at least one compliant inflatable member coupled at a first attachment position to the radially non-compliant portion and at a second attachment position to the radially compliant portion, the inflatable member being adapted to be coupled to a pressure source and to be inflated radially outwardly from the body portion.

2. The sheath assembly according to claim 1 wherein the body portion has an open end adapted to receive the insertion tube, and wherein the radially compliant portion includes an enclosed distal end proximate a distal end of the insertion tube when the insertion tube is received into the body portion.

3. The sheath assembly according to claim 2 wherein the radially non-compliant portion is coupled to the radially compliant portion and disposed between the radially compliant portion and the open end.

4. The sheath assembly according to claim 1 wherein the radially non-compliant portion comprises a compliant tubing having at least one reinforcing spring member disposed therein.

5. The sheath assembly according to claim 1 wherein the radially non-compliant portion comprises a radially non-compliant sleeve.

6. The sheath assembly according to claim 1 wherein the radially non-compliant portion is at least partially longitudinally non-compliant.

7. The sheath assembly according to claim 1 wherein the inflatable member has an inner chamber and the radially non-compliant portion has an inflation port disposed therethrough in fluid communication with the inner chamber.

8. The sheath assembly according to claim 1 wherein the inflatable member comprises a circumferential inflatable member circumferentially disposed about the body portion.

9. The sheath assembly according to claim 1 wherein the enclosed distal end includes a transparent window portion proximate the distal end of the insertion tube when the insertion tube is received into the body portion.

10. The sheath assembly according to claim 1 wherein the inflatable member includes a sheet of compliant material having a first edge coupled to the body portion at a first longitudinal position and a second edge attached to the body portion at a second longitudinal position.

11. The sheath assembly according to claim 10 wherein at least one of the first and second edges is invertedly attached to the body portion.

12. A method of using an endoscope assembly within an internal passage, comprising:
    positioning a sheath assembly at least partially onto an insertion tube of an endoscope, the sheath assembly including a body portion at least one radially expandable inflatable member coupled to the body portion, and at least one expansion-inhibiting mechanism;
    at least partially inserting the insertion tube and sheath into the internal passage; and at least partially inflating the radially expandable member; and at least partially inhibiting a longitudinal expansion of at least part of the body portion of the sheath assembly using the at least one expansion-inhibiting mechanism.

13. The method according to claim 12 wherein positioning a sheath assembly at least partially onto an insertion tube comprises positioning a sheath assembly having at least one expansion-inhibiting mechanism including a non-compliant member coupled to at least one of the inflatable member and the body portion.

14. The method according to claim 12 wherein positioning a sheath assembly at least partially onto an insertion tube comprises positioning a sheath assembly having at least one expansion-inhibiting mechanism including a non-compliant sleeve member extending between first and second longitudinal positions of the body portion.

15. The method according to claim 12 wherein positioning a sheath assembly at least partially onto an insertion tube comprises positioning a sheath assembly having a working channel extending along the body portion, the at least one expansion-inhibiting mechanism comprising a non-compliant portion of the working channel.

16. The method according to claim 12 wherein positioning a sheath assembly at least partially onto an insertion tube comprises positioning a sheath assembly including a body portion having a compliant first portion and a non-compliant second portion, the inflatable member being coupled to the non-compliant second portion.

17. The method according to claim 12 wherein positioning a sheath assembly at least partially onto an insertion tube comprises positioning a sheath assembly including a body portion having a compliant first portion and a non-compliant second portion, the inflatable member being coupled to the non-compliant second portion, and wherein the compliant first portion includes the enclosed distal end.

18. The method according to claim 12 wherein positioning a sheath assembly at least partially onto an insertion tube comprises positioning a sheath assembly including a body portion having a first portion and a second portion, the first portion being longitudinally stretched when the insertion tube is received into the body portion, the inflatable member being coupled to the first longitudinally-stretched portion.

19. The method according to claim 12 wherein positioning a sheath assembly at least partially onto an insertion tube comprises positioning a sheath assembly including a body portion having a first portion and a second portion, the first portion being longitudinally stretched when the insertion tube is received into the body portion, the first longitudinally stretched portion including at least one reinforcing spring member, the inflatable member being coupled to the first longitudinally-stretched portion.

20. The method according to claim 12 wherein positioning a sheath assembly at least partially onto an insertion tube comprises positioning a sheath assembly including a pressure relief device fluidly coupled to the inflatable member, the pressure relief device being adapted to maintain a desired pressure within the inflatable member.

21. The method according to claim 12 wherein positioning a sheath assembly at least partially onto an insertion tube comprises positioning a sheath assembly including at least one first detent mechanism adapted to be engaged with at least one second detent mechanism on the insertion tube.

22. The method according to claim 12 wherein positioning a sheath assembly at least partially onto an insertion tube comprises positioning a sheath assembly including at least one partially annular, inwardly projecting ridge adapted to be engaged with an at least partially annular groove disposed in the insertion tube.

23. The method according to claim 12 wherein positioning a sheath assembly at least partially onto an insertion tube comprises positioning a sheath assembly including at least one partially spherical, inwardly projecting bump adapted to be engaged with an at least partially spherical dimple disposed in the insertion tube.

* * * * *